(12) United States Patent
Zhou (10) Patent No.: US 11,160,842 B2
(45) Date of Patent: Nov. 2, 2021

(54) DRUG OR HEALTH CARE PRODUCT PREVENTING OR TREATING LIVER AND KIDNEY DAMAGE-RELATED DISEASES AND USE THEREOF

(71) Applicant: Guangxi HebaBiz Pharmaceutical Technology Co., Ltd., Guangxi (CN)

(72) Inventor: James Zhou, Beijing (CN)

(73) Assignee: GUANGXI HEBABIZ PHARMACEUTICAL TECHNOLOGY CO., LTD, Guangxi (CN)

( * ) Notice: Subject to any disclaimer, the term of this patent is extended or adjusted under 35 U.S.C. 154(b) by 532 days.

(21) Appl. No.: 15/526,870

(22) PCT Filed: Apr. 29, 2015

(86) PCT No.: PCT/CN2015/000296
§ 371 (c)(1),
(2) Date: May 15, 2017

(87) PCT Pub. No.: WO2016/074333
PCT Pub. Date: May 19, 2016

(65) Prior Publication Data
US 2019/0167752 A1    Jun. 6, 2019

(30) Foreign Application Priority Data
Nov. 15, 2014 (CN) .......................... 201410646052.6

(51) Int. Cl.
| | | |
|---|---|---|
| A61K 36/00 | (2006.01) | |
| A61K 36/8969 | (2006.01) | |
| A61K 36/752 | (2006.01) | |
| A61K 36/804 | (2006.01) | |
| A61K 36/815 | (2006.01) | |
| A61K 36/8968 | (2006.01) | |
| A61K 36/232 | (2006.01) | |
| A61K 36/233 | (2006.01) | |
| A61K 36/236 | (2006.01) | |
| A61K 36/287 | (2006.01) | |
| A61K 36/482 | (2006.01) | |
| A61K 36/71 | (2006.01) | |
| A61K 36/888 | (2006.01) | |
| A61P 1/16 | (2006.01) | |
| A61P 13/12 | (2006.01) | |

(52) U.S. Cl.
CPC ........ *A61K 36/8969* (2013.01); *A61K 36/232* (2013.01); *A61K 36/233* (2013.01); *A61K 36/236* (2013.01); *A61K 36/287* (2013.01); *A61K 36/482* (2013.01); *A61K 36/71* (2013.01); *A61K 36/752* (2013.01); *A61K 36/804* (2013.01); *A61K 36/815* (2013.01); *A61K 36/888* (2013.01); *A61K 36/8968* (2013.01); *A61P 1/16* (2018.01); *A61P 13/12* (2018.01)

(58) Field of Classification Search
None
See application file for complete search history.

(56) References Cited

FOREIGN PATENT DOCUMENTS

| | | |
|---|---|---|
| CN | 1745828 A | 3/2006 |
| CN | 100415275 C | 9/2008 |
| CN | 101716280 A | 6/2010 |
| CN | 101972340 A | 2/2011 |
| CN | 102138661 A | 8/2011 |
| CN | 101940758 B | 1/2012 |
| CN | 102813857 A | 12/2012 |
| CN | 102526473 B | 5/2013 |
| CN | 103330785 A | 10/2013 |
| CN | 103463404 A | 12/2013 |
| CN | 104000128 A | 8/2014 |
| JP | 2007153888 A | 6/2007 |

OTHER PUBLICATIONS

Japanese office action for patent application No. 2017-544807 dated Nov. 21, 2018.
Examination report for Australian application No. 2015345884 dated Jul. 22, 2020.
Further examination report for Australian application No. 2015345884 dated Aug. 4, 2020.

*Primary Examiner* — Russell G Fiebig
(74) *Attorney, Agent, or Firm* — Bachman and Lapointe PC; George Coury (57) ABSTRACT

A traditional Chinese medicine composition for protecting the liver and kidney and a preparation method and use thereof. The composition is composed of 100-200 parts of *Polygonatum odoratum*, 100-200 parts of *fructus lycii*, 80-160 parts of *radix ophiopogonis*, 70-130 parts of *Angelica sinensis*, 70-130 parts of *semen cassiae*, 70-130 parts of white peony root, 70-130 parts of dried orange peel, 70-130 parts of prepared *rehmannia* root, 70-130 parts of *chrysanthemum*, 30-70 parts of rhizome *chuanxiong*, 20-40 parts of Irkutsk *anemone* rhizome, and 10-20 parts of *bupleurum* by weight.

9 Claims, 8 Drawing Sheets

DRUG OR HEALTH CARE PRODUCT PREVENTING OR TREATING LIVER AND KIDNEY DAMAGE-RELATED DISEASES AND USE THEREOF

FIELD OF TECHNOLOGY

The invention belongs to the technical field of traditional Chinese medicine. In particular, the invention relates to a preparation method and its application of a traditional Chinese medicine composition for protecting liver and kidney.

BACKGROUND TECHNOLOGY

After thousands of years of development of traditional Chinese medicine theory, broad and profound, advocate the overall treatment, drug compatibility. However, the inventors found that traditional Chinese medicine has two main drawbacks. First, there are so many kinds of crude drugs, which are not conducive to the stability of drug quality, and it is very complex in the section of drug test, which is not conducive to the promotion of industrialization; second, the effect is unstable, and due to lack of support of statistical data, is done mostly by experience.

For example, China patent application No. 200510012859 discloses a purple eye liver soup based composition to purple eye, with purple eye the main drug, and with 24 kinds of other drugs such as *Radix Angelicae sinensis*, White peony root, *Rhizoma Chuanxiong*, prepared *rehmannia* root, black sesame, radices *ophiopogonis*, papaya, *semen zizyphi spinosae*, *Fructus lycii*, *Chrysanthemum*, *radix sileris*, *radix asparagi*, *Dioscorea opposita* Thunb., *Poria*, *plantago* seed, *Platycodon grandiflorum*, *Bupleurum*, dendrobe, *asarum*, *Schisandra chinensis*, Polygalae root, fried Zaoren, licorice.

Chinese patent application No. 200910214092 discloses a pharmaceutical composition for treating liver cancer, including the *Radix Ginseng Rubra* prescription, *astragalus*, *Codonopsis*, *Poria*, *radix rehmanniae*, *Radix Scrophulariae*, *Fructus lycii*, Cortex Moutan, *Radix Glehniae*, asparagus cochinchinensis, *Radix Ophiopogonis*, turtle shell, *Cornus officinalis*, *Polygonum multiflorum*, *Radix Angelicae sinensis*, *Radix Paeoniae* wine *alba*, *semen zizyphi spinosae*, *semen* boitae, *Salvia miltiorrhiza*, *Bupleurum*, ochre, *rhizoma polygonati*, white *atractylodes* rhizome, lotus seeds, longan pulp, licorice, honeysuckle, *forsythia*, pseudo-*ginseng*, pangolin, safflower, peach, frankincense, myrrh, cinnabar, amber, totally 36 medicine herbs.

Chinese patent application No. 201010258165 discloses a traditional Chinese medicine composition for a the treatment of hepatitis B, and the clinical symptoms caused by hepatitis B virus, which is composed of the following 24 kinds of Chinese medicine raw materials: *Radix Angelicae sinensis*, white *atractylodes* rhizome, rhubarb, turmeric, *Ganoderma lucidum*, *Radix Ophiopogonis*, Prepared *rehmannia* root, Cortex Phellodendri, fried yam, *Cornus officinalis Rhizoma*, *chuanxiong*, *Poria*, Chinese wolfberry, fried chicken, *Morinda officinalis*, Cortex Moutan, Patrinia, dandelion, *forsythia*, wild hawthorn, *Radix* Scutellariae, *Radix* Glycyrrhizae, fried White peony root, *Schisandra chinensis*.

Chinese patent application No. 201210075569 discloses a medicament for the treatment of chronic hepatitis B, which is composed of the following 16 crude drugs: *Radix Ophiopogonis*, made from dandelion, *radix* rehmanniae, *Plantago*, wormwood, phellodendron, medlar, *Platycodon grandiflorum*, *Radix Angelicae sinensis*, rehmannia, *Gallus gallus*, *Portulaca grandiflora*, *Belamcanda chinensis*, *Radix* Scrophulariae, White peony root and *radix* rubiae.

However, after the inventor's long-term research and practice in traditional Chinese medicine theory and modern pharmacy, the inventor surprisingly discovered a new formula of traditional Chinese medicine, which can reduce drug types, and significantly change the drug ratio and the relationship between monarch, meantime the effect is good and stable in protecting the liver and/or kidney (such as for the prevention or treatment of liver injury and/or renal damage). In addition, the inventor has explored the preparation process of the medicament, which can be directly amplified and used for the manufacture on a large scale, and this is particularly beneficial for the small amount of laboratory preparation for research and large-scale preparation of pharmaceutical companies.

CONTENTS OF THE INVENTION

The aim of the invention is to provide a new traditional Chinese medicine composition for protecting liver and kidney. In addition, the invention is also to provide a preparation method and application of the traditional Chinese medicine composition.

Specifically, in the first aspect, the invention provides a traditional Chinese medicine composition for the protection of liver and kidney (especially for the protection of the liver), the weight of the crude drug made by the following:

100~200 parts of *Polygonatum odoratum*, 100~200 parts of *fructus lycii*, 80~160 parts of *radix ophiopogonis*, 70~130 parts of *radix angelicae sinensis*, 70~130 parts of *semen cassiae*, 70~130 parts of white peony root, 70~130 parts of dried orange peel, 70~130 parts of prepared *rehmannia* root, 70~130 parts of *chrysanthemum*, 30~70 parts of *rhizoma chuanxiong*, 20~40 parts of Irkutsk *anemone* rhizome, and *bupleurum*.

In this paper, *Polygonatum odoratum* (*Polygonatum*), *fructus lycii* (*Lycium*), *radix ophiopogonis* (Ophiopogon), *radix angelicae sinensis* (*Angelica*), *semen cassiae* (*Cassia*), white peony root (*Paeonia*), dried orange peel (*Citrus*), prepared *rehmannia* root (*Rehmannia*), *chrysanthemum* (*Chrysanthemum*), *rhizoma chuanxiong* (*Ligusticum*), Irkutsk *anemone* rhizome (*Anemone*), and *bupleurum* (*Bupleurum*) can be obtained through marketing channels (raw material). Although there are some aliases or synonyms, the technical personnel of this field can purchase the corresponding drug by the name.

Chinese medicine composition preferably referred in the first anthology of the present invention is made by weight of part crude drugs:

120~180 parts of *Polygonatum odoratum*, 120~180 parts of *fructus lycii*, 100~150 parts of *radix ophiopogonis*, 80~120 parts of *radix angelicae sinensis*, 80~120 parts of *semen cassiae*, 80~120 parts of white peony root, 80~120 parts of dried orange peel, 80~120 parts of prepared *rehmannia* root, 80~120 parts of *chrysanthemum*, 40~60 parts of *rhizoma chuanxiong*, 25~35 parts of Irkutsk *anemone* rhizome, and 12~18 parts of *bupleurum*.

Chinese medicine composition is more preferably referred in the first anthology of the present invention are made by weight of part crude drugs:

140~160 parts of *Polygonatum odoratum*, 140~160 parts of *fructus lycii*, 110~130 parts of *radix ophiopogonis*, 90~110 parts of *radix angelicae sinensis*, 90~110 parts of *semen cassiae*, 90~110 parts of white peony root, 90~110 parts of dried orange peel, 90~110 parts of prepared *rehmannia* root, 90~110 parts of *chrysanthemum*, 45~55 parts of *rhizoma chuanxiong*, 28~33 parts of Irkutsk *anemone* rhizome, and 14~16 parts of *bupleurum*.

In the embodiments of the invention, Chinese medicine composition are made by weight of part crude drugs: 150 parts of *Polygonatum odoratum*, 150 parts of *fructus lycii*, 120 parts of *radix ophiopogonis*, 100 parts of *radix angelicae sinensis*, 100 parts of *semen cassiae*, 100 parts of white peony root, 100 parts of dried orange peel, 100 parts of prepared *rehmannia* root, 100 parts of *chrysanthemum*, 50 parts of *rhizoma chuanxiong*, 30 parts of Irkutsk *anemone* rhizome, and 15 parts of *bupleurum*.

The traditional Chinese medicine composition of the first aspect of the invention is also preferably composed of the following components:

The volatile oil of *radix angelicae sinensis, rhizoma chuanxiong, chrysanthemum, bupleurum*, Irkutsk *anemone* rhizome and dried orange peel, Non-alcohol precipitation of water soluble matter of *radix angelicae sinensis, rhizoma chuanxiong, chrysanthemum, bupleurum*, Irkutsk *anemone* rhizome and dried orange peel for extracting volatile oil, Non-alcohol precipitation of water soluble matter of *radix angelicae sinensis, rhizoma chuanxiong, chrysanthemum, bupleurum*, Irkutsk *anemone* rhizome and dried orange peel for Extracting volatile oil and extracting water soluble matter, and Non-alcohol precipitation of water soluble matter of *Polygonatum odoratum, fructus lycii, radix ophiopogonis, semen cassiae*, white peony root and prepared *rehmannia* root.

Further, in the first aspect of the invention, the volatile oil is prepared by adding water to the distillation and retaining the volatile oil.

Also preferably in the first aspect of the invention, the aqueous solution is prepared by adding water to the distilled water and retaining the water solution.

Also the traditional Chinese medicine composition referred in the first aspect of the invention, the water were extracted by decoction and keeping the water solution preparation. The more preferably, the number of decoction with water is 1~3 times, preferably 2 times; and/or, each time for the decoction is 0.5~3 hours, preferably 1~1.5 hours.

In the first aspect of the invention, the non alcohol precipitate is prepared by increasing the concentration of the alcohol and retaining the alcohol soluble substance.

Also preferably in the present invention, the first aspect of the traditional Chinese medicine composition, the alcohol is ethanol, more preferably is 60% (V/V) ethanol.

And also the first anthology of traditional Chinese medicine composition by the preparation method comprises the following steps:

(1) Smash and mix *radix angelicae sinensis, rhizoma chuamdong, chrysanthemum, bupleurum*, Irkutsk *anemone* rhizome and dried orange peel, add water and perform distillation, retention of volatile oil, water solution and dregs not dissolve in water;

(2) Mix dregs obtained in step (1) and *Polygonatum odoratum, fructus lycii, radix ophiopogonis, semen cassiae*, white peony root and prepared *rehmannia* root, decoct them with water, and then mix the filtrate and the aqueous solution obtained from step (1), concentrate, increase the alcohol concentration, the supernatant was recovered after alcohol, filtered and concentrated, clear paste; and (3) Mix the clear paste obtained from step (2) and volatile oil obtained from step (1).

In the second aspect, the invention provides a preparation method of the traditional Chinese medicine composition, which is the first aspect of the invention:

(1) Smash and mix *radix angelicae sinensis, rhizoma chuanxiong, chrysanthemum, bupleurum*, Irkutsk *anemone* rhizome and dried orange peel, add water and perform distillation, retention of volatile oil, water solution and dregs not dissolve in water;

(2) Dregs obtained in step (1) and *Polygonatum odoratum, fructus lycii, radix ophiopogonis, semen cassiae*, white peony root and prepared *rehmannia* root were mixed and decocted with water, filtrate and aqueous solution obtained from step (1) were mixed, concentrated to increase the alcohol concentration, the supernatant was recovered after alcohol, filtered and concentrated, clear paste; and (3) Mix the clear paste obtained from step (2) and volatile oil obtained from step 1.

The method can be used to enlarge the scale of production. Therefore, preferred in the second aspect of the invention of the preparation method, the crude drug is large-scale production level, such as the weight of *Polygonatum odoratum* is more than 10 kg, preferably more than 50 kg, more preferably greater than 100 kg, which can determine the weight of other drugs.

In the third aspect, the invention provides a traditional Chinese medicine preparation for protecting liver and kidney (especially for protecting liver), which comprises a first aspect of the invention, a traditional Chinese medicine composition, and a pharmaceutical acceptable carrier.

In this paper, the "pharmaceutical acceptable carrier" refers to a pharmaceutically acceptable non-toxic solid, semi-solid or liquid filling agent, diluent, adjuvant, package material or other pharmaceutical excipients. The technical staff in this field can make the traditional Chinese medicine composition of the first aspect of the invention into various formulations according to the purpose of the treatment and the route of administration. The composition preferably unit dosage forms, such as tablets, pills, capsules membrane agent (including sustained release or delayed release set form), powder, granule, tincture, syrup and emulsion agent, solution or suspension, or liquid aerosol spray drops, injection, automatic injection device or suppository in specific. In the embodiment of the invention, a pharmaceutically acceptable carrier includes sugar, honey and/or Ethylparaben.

The traditional Chinese medicine preparation in the third aspects of the invention is an oral preparation, such as oral liquid.

The traditional Chinese medicine preparation in the third aspects of the invention is prepared by a method comprising the steps of the following steps:

(1) Smash and mix *radix angelicae sinensis, rhizoma chuanxiong, chrysanthemum, bupleurum*, Irkutsk *anemone* rhizome and dried orange peel, and add water to distill and retain the volatile oil, aqueous solution and dregs not dissolved in water;

(2) Dregs obtained in step (1) and *Polygonatum odoratum, fructus lycii, radix ophiopogonis, semen cassiae*, white peony root and prepared *rehmannia* root were mixed and decocted with water, the filtrate and the aqueous solution obtained in step (1) were mixed, concentrate to increase the alcohol concentration, the supernatant was recovered after alcohol, filtered and concentrated, clear paste was obtained; and, (3) Mix the clear paste obtained from step (2) and volatile oil obtained from step (1), and the carrier acceptable in pharmacy.

In the fourth aspect, the invention provides a preparation method of the traditional Chinese medicine preparation in third aspects:

(1) Smash and mix *radix angelicae sinensis, rhizoma chuanxiong, chrysanthemum, bupleurum*, Irkutsk *anemone* rhizome and dried orange peel, add water to distill, retain the volatile oil, water solution and dregs not dissolve in water;

(2) Dregs obtained in step (1) and *Polygonatum odoratum, fructus lycii, radix ophiopogonis, semen cassiae,* white peony root and prepared *rehmannia* root were mixed and decocted with water, the filtrate and the aqueous solution obtained in step (1) were mixed, concentrate to increase the alcohol concentration, the supernatant was recovered after alcohol, filtered and concentrated, clear paste was obtained; and, (3) Mix the clear paste obtained from step (2) and volatile oil obtained from step (1), and the carrier acceptable in pharmacy.

The method can be used to enlarge the scale of production scale level. Therefore, preferably in the preparation method of the fourth aspect of the invention, the crude drug is large-scale production level, for example, the weight of *Polygonatum odoratum* is more than 10 kg, preferably more than 50 kg, more preferably greater than 100 kg, which can also determine the weight of other drugs.

In the fifth aspect, the invention provides the application of the traditional Chinese medicine composition of the first aspect of the invention in the preparation of a medicament for protecting the liver and/or kidney.

Preferably in application of the fifth aspect of the invention, the protection of liver and kidney is the prevention or treatment of liver injury and/or renal injury, especially liver injury. Preferably the liver injury and/or renal injury of liver and/or renal toxicity of chemical induced liver injury and/or further kidney damage. Further, the preferred liver and/or renal toxicity chemical substances are alcohol, carbon tetrachloride, cyclophosphamide, isoniazid and rifampicin.

In the sixth aspect, the invention provides the application of a traditional Chinese medicine composition of the first aspect of the present invention in preparation for medicine to reduce cholesterol, triglyceride, low density lipoprotein, creatinine, urea nitrogen, uric acid, to improve the level of high density lipoprotein, to reduce fatty liver symptoms.

The invention has the advantage that the traditional Chinese medicine composition and traditional Chinese medicine preparation have good effect in protecting liver and kidney, are suitable for the prevention or treatment of liver injury and/or renal injury caused by extensive hepatic and/or renal toxicity of chemical, the therapeutic effect is effective and stable, reduce cholesterol, triglyceride, low density lipoprotein protein, creatinine, urea nitrogen, and/or uric acid levels, improve the level of high density lipoprotein, and reduce symptoms of fatty liver; the preparation for the traditional Chinese medicine composition of the invention is easy to standardization and quality control, and is especially suitable for amplification and large-scale production.

For easy understanding, the following will describe the invention according to specific examples and figures. In particular, the description is only illustrative description which does not mean a limit to the scope of the invention. In addition, the references cited in this invention are included in this article, as if they are described completely herein.

DESCRIPTION OF DRAWINGS

In FIG. 1, FIG. 3, FIG. 5, FIG. 7, compared with blank control group, #$p<0.05$, ##$p<0.01$, ###$p<0.001$; compared with model group, *$p<0.05$, $p<0.01$, *$p<0.001$.

DETAILED DESCRIPTION

Specific Implementation Modalities

Below through an example to further elaborate the preparation of the invention of Chinese medicine preparation and application, but not in any way to limit the scope of the present invention.

Example 1 the Lab Preparation of Traditional Chinese Medicine Oral Liquid of this Invention Take *radix angelicae sinensis* 100 g, *rhizoma chuanxiong* 50 g, *chrysanthemum* 100 g, *bupleurum* 15 g, Irkutsk *anemone* rhizome 30 g and dried orange peel 100 g. After cataclasm, add 2000 mL of water and distil it at 95-100° C., collect distilled volatile oil, filter distilled material in container, reserve water solution, after filtration, obtain the residue the residue and mix with the Prepared *rehmannia* root 100 g, White peony root 100 g, *Semen Cassiae* 100 g, *Polygonatum odoratum* 150 g, *Fructus*, lycil 150 g and *Radix Ophiopogonis* 120 g; accept decoction two times, the first time adds 6.7 L water, boiling 1.5 hours; the second time adds 5.7 L water, boiling 1 hours, collect two times of decoction and obtain the decoction liquid; then after filtration, combine the filtrate and the aqueous solution and concentrate to the clear paste with relative density 1.15 (60 C), adding ethanol to the alcohol content is 60% (V/V), stand for 48 hours, obtain the supernatant and vacuum recover ethanol to no alcohol taste, and add two times of water (V/V) and mix it, stand for 48 hours, filtering, the filtrate is concentrated to the clear paste with relative density is 1.07 (60 C), add honey 300 g, Ethylparaben 0.3 g (when necessary, use a small amount of ethanol to dissolve Ethylparaben) and the volatile oil, adjust it to pH 6 with 10% (W/W) sodium hydroxide solution, add purified water to the total amount of 1000 mL, stir, filtering, and obtain the product.

Example 2 Large Scale Preparation of Traditional Chinese Medicine Oral Liquid of this Invention The inventor worked out that the laboratory preparation methods can be directly amplified for large-scale production, no significant difference in drug efficacy and laboratory preparation methods to obtain drugs prepared. Specifically, take *radix angelicae sinensis* 100 kg, *rhizoma chuanxiong* 50 kg, *chrysanthemum* 100 kg, *bupleurum* 15 kg, Irkutsk *anemone* rhizome 30 kg and dried orange peel 100 kg, After cataclasm, add 5 times of water and distil it at 95-100° C., collect distilled the volatile oil 500 mL, filter distilled material in container, reserve water solution 1200 L, after filtration, obtain the residue and mix with the Prepared *rehmannia* root 100 kg, White peony root 100 kg, *Semen Cassiae* 100 kg, *Polygonatum odoratum* 150 kg, *Fructus*, lycil 150 kg and *Radix Ophiopogonis* 120 kg; accept decoction two times, the first time adds 6700 L water, boiling 1.5 hours; the second time adds 5660 L water, boiling 1 hours, collect two times of decoction and obtain the decoction liquid; then after filtration, combine the filtrate and the aqueous solution and concentrate to the clear paste with relative density 1.15 (60° C.), adding ethanol to the alcohol content is 60% (V/V), stand for 48 hours, obtain the supernatant and vacuum recover ethanol to no alcohol taste, and add two times of water (V/V) and mix it, stand for 48 hours, filtering, the filtrate is concentrated to the clear paste with relative density is 1.07 (60 C), add sucrose 300 kg, honey 1.5 g, Ethylparaben 0.3 kg (when necessary, use a small amount of ethanol to dissolve Ethylparaben) and the volatile oil, adjust it to pH 6 with 10% (W/W) sodium hydroxide solution, add purified water to the total amount of 1000 L, stir, filtering, and obtain the product.

Example 3 the Effect of the Traditional Chinese Medicine Oral Liquid on Alcoholic Liver Injury Rats Take 46 SD rats to adapt to the environment after a week, which were randomly divided into 6 groups (blank, control group 6, the other 8 rats in each group), respectively: blank control group (Control), model group (Model), silymarin (positive drug control) group (purchased from Madaus AG,) the invention low dose group (GX001-1), the invention middle dose group (GX001-2.5), the invention high dose group (GX001-5). in the silymarin group rats were given 100 mg/kg silymarin daily, the invention low, middle and high dose group rats were given 1 ml/kg, 2.5 ml/kg and 5 ml/kg Chinese medicine oral liquid prepared in example 2, blank control group and model group rats were given 10 ml/kg saline daily. From the eleventh day, 4H after drug administration, rats in the blank control group were treated with 14 ml/kg saline via gavage, rats in other groups were respectively treated with 56 degree Red Star Erguotou liquor 14 ml/kg, lasting 4 weeks as above. 4 h after the last time of liquor dosage, all the rats were weighed and sacrificed by cervical dislocation, blood was collected and centrifuged, serum were removed to quantification of serum alanine aminotransferase (ALT), aspartate aminotransferase (AST) activity, total bilirubin (TB) and total triglyceride (TG) content. The liver tissues were preserved in 10% buffered formaldehyde solution and then stained with hematoxylin and eosin (H and E) necrosis, hydropic degeneration, inflammatory cell infiltration and other pathological changes were observed under light microscpoe.

Figure 1:
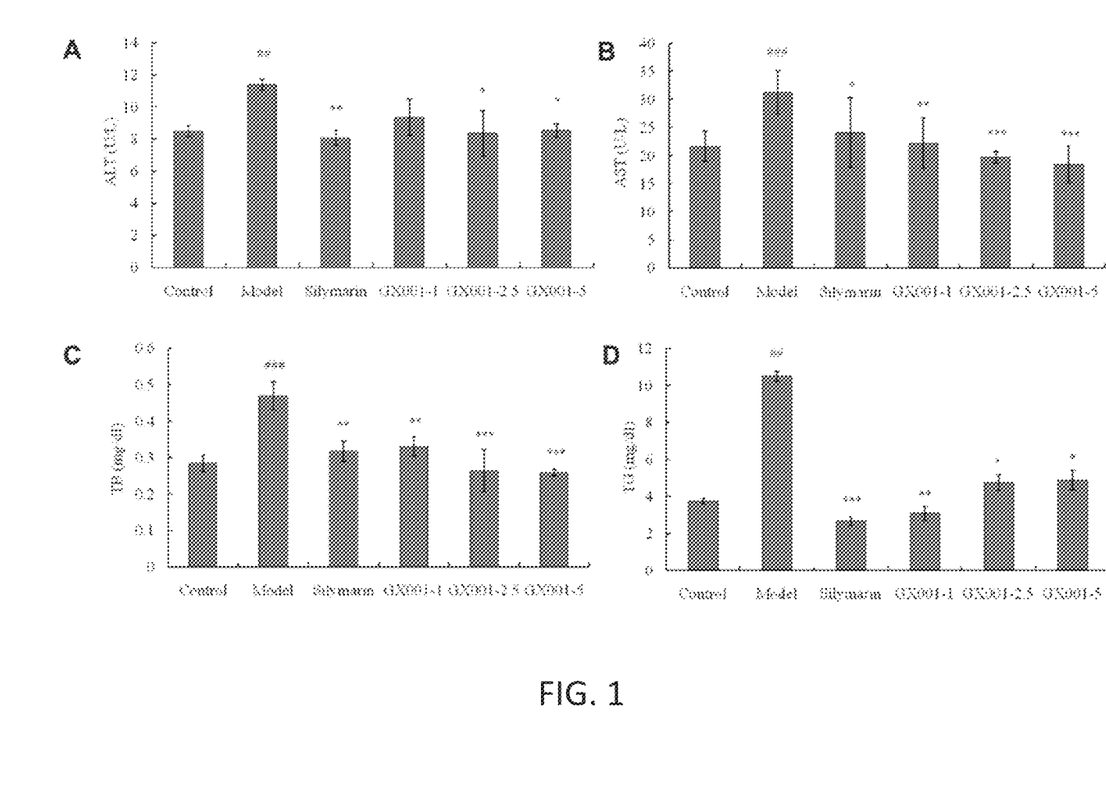
FIG. 1 shows the effect of exemplary drug in the invention on the serum and related liver biochemical indexes of alcoholic liver injury rat model, including (A) serum ALT activity of alcoholic liver injury rat model; (B) serum AST activity of alcoholic liver injury rat model; C) serum TB level of alcoholic liver injury rat model; (D) serum TG level of alcoholic liver injury rat model.
Figure 2:
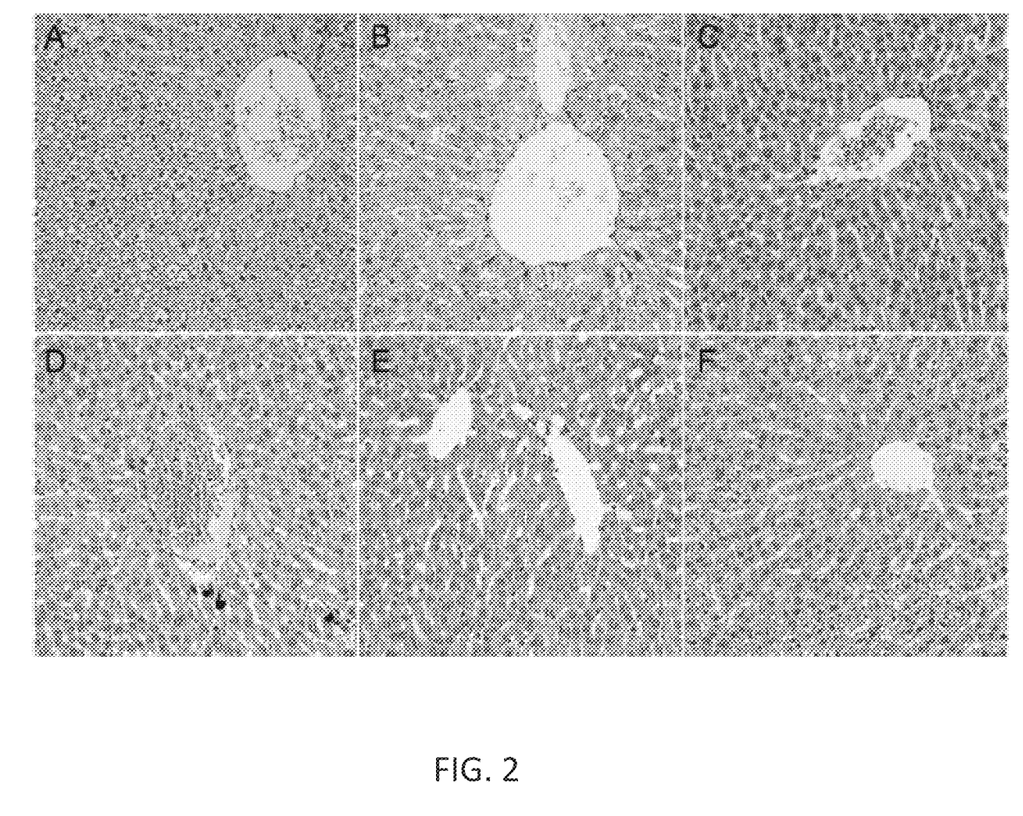
FIG. 2 shows the HE staining of liver tissue of alcoholic liver injury rat model (200×), including, (A) blank control group; (B) model group; (C) silymarin group; (D) the invention low dose group; (E) the invention middle dose group; (F) the invention high dose group.

The results are indicated in FIG. 1 and FIG. 2. As shown in FIG. 1, compared with the blank control group, the activity of ALT, AST increased significantly in the model group rats; the content of TB, TG were significantly increased; compared with model group, the ALT/AST activity of silymarin group and each oral liquid group rats serum decreased significantly, TB, TG content decreased significantly. It indicates that the traditional Chinese medicine oral liquid can effectively alleviated the abnormal liver function and lipid metabolism disorder caused by chronic alcohol intake.

As shown in FIG. 2, HE staining of liver tissues of alcoholic liver injury rats were observed. The blank control group (A) showed complete structure of hepatic lobules, integrated central vein cord, orderly arranged hepatic cables, uniform size, central nucleus, pink cytoplasm; the model group (B) showed disorder of hepatic lobules, the cell nucleus were located near the cell membrane, inflammatory cell infiltration, cell necrosis, nuclear fusion, hydropic degeneration of hepatic cells; the invention low dose group (D) and middle dose group (E) showed normal structure of hepatic lobules, the cell nucleus were located central, only a few necrotic cells in central vein; the invention high dose group (F) and silymarin group (C) showed tidy arranged hepatic lobules, uniform size, normal structure, no necrosis/degeneration, exerted significant improvements compared with that of model group.

Example 4 the Efficacy of the Traditional Chinese Medicine Oral Liquid for the Treatment of Acute Liver Injury Induced by Cyclophosphamide in Mice Take 60 BALB/c mice and divide them into 6 groups (10 per group), respectively: blank control group (Control), model group (Model), silymarin (positive drug control) group (purchased from Madaus AG,) the invention low dose group (GX001-2.5), the invention middle dose group (GX001-5), the invention high dose group (GX001-10). The blank control group and model group received saline 200 ml/kg daily by gavage. In silymarin group, 200 mg/kg daily dose of silymarin was administrated, the invention low, middle and high dose group every day respectively received 2.5 ml/kg, 5 ml/kg and 10 ml/kg oral liquid prepared in accordance with the example 2 cases (ig), 1 time per day, lasting 7 days. Except the blank group, the other groups were treated with cyclophosphamide (80 m/kg, i.p.) in first, 3, 5, 7 days. 24 h after the last administration, mice were sacrificed by cervical dislocation; animals were fasting 16 hours before sacrificed, but water was given. The eyeballs were extracted and blood was drawn and centrifuged, serum was removed to quantification of serum alanine aminotransferase (ALT), aspartate aminotransferase (AST) activity, the total bilirubin (TB) and total triglyceride (TG) content. A part of liver tissue were washed with ice physiological saline to remove blood, absorbed water and weighing, take part of the liver with saline ice homogenates prepared 10% liver homogenate, 4 C, 5000 rpm centrifugation for 5 min, determined the liver tissue homogenate (MDA) content according to instructions. A part of liver tissue were preserved in 10% buffered formaldehyde solution and then stained with hematoxylin and eosin (H and E), observe necrosis, vasculopathy and other pathological changes under light microscpoe.

Figure 3:
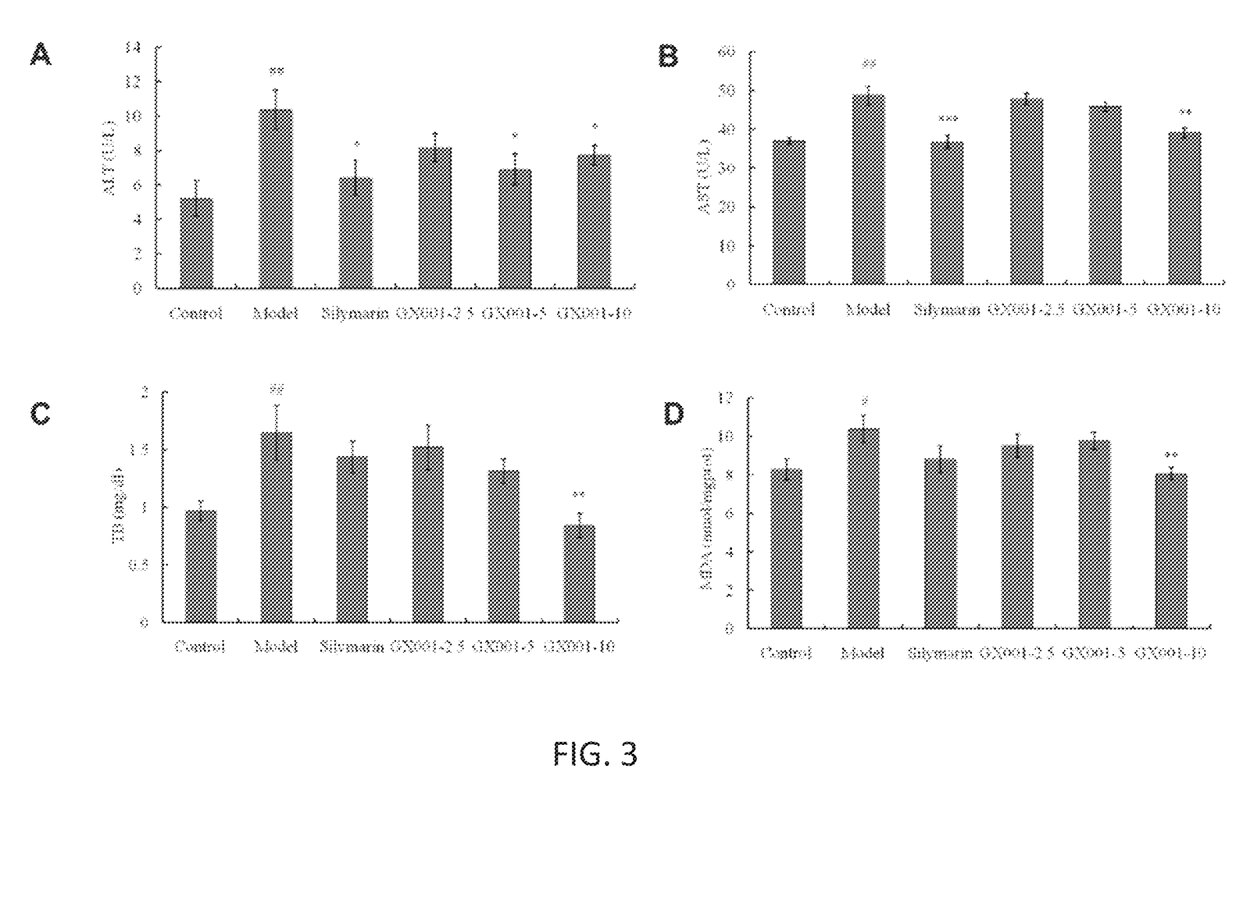
FIG. 3 shows the effect of the exemplary drug on serum and liver biochemical indexes of cyclophosphamide induced liver injury mice model including (A) serum ALT activity of cyclophosphamide induced liver injury mice model (B) serum AST activity of cyclophosphamide induced liver injury mice model; (C) serum TB content of cyclophosphamide induced liver injury mice; (D) liver MDA content of cyclophosphamide induced liver injury mice.
Figure 4:
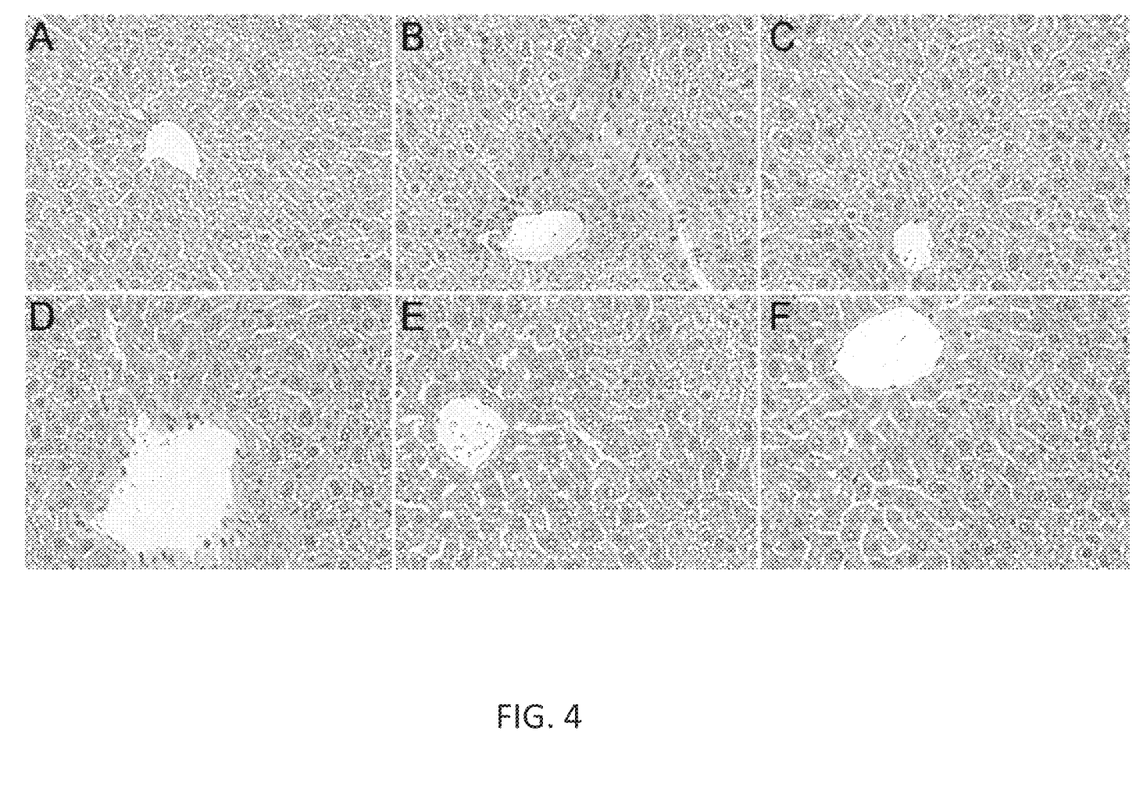
FIG. 4 shows HE staining of liver tissue of cyclophosphamide induced liver injury mice (400×), including, (A) blank control group; (B) model group; (C) silymarin group; (D) the invention low dose group; (E) the invention middle dose group; (F) the invention high dose group.

The results are indicated in FIG. 3 and FIG. 4. As shown in FIG. 3, compared with the blank control group, in the model group, the activity of serum ALT, AST increased significantly; the content of TB, MDA were significantly increased; compared with the model group, the silymarin group and the each invention group ALT/AST activity decreased significantly. TB, MDA content decreased significantly. It indicates that the traditional Chinese medicine oral liquid can effectively improve the liver function abnormality caused by cyclophosphamide.

As shown in FIG. 4, HE staining of liver tissues of cyclophosphamide induced liver injury mice were observed. blank control group (A) hepatic lobules is clear, the central vein cord is in integrity, liver cells arrange in neat rows, There was no obvious expansion of hepatic sinus, no expansion and fibrosis of portal tract, no interface inflammation, liver cell had no obvious necrosis, regeneration and degeneration; model group (B) showed congestion in the center of hepatic lobule, obvious vascular sclerosis, but complete structure of hepatic cords; silymarin group (C) orderly arranged hepatic cords, complete structure of hepatic lobules, indicating positive drug silymarin is effective, the invention middle dose group (E), high dose group (F) can be observed in complete structure of hepatic lobules, no obvious vascular lesions; the invention low dose group (D) showed hepatic lobules proliferation, but the treatment effect is not obvious compared with the high/middle dose group.

Example 5 the Effects of the Traditional Chinese Medicine Oral Liquid on the Acute Liver Injury Induced by Carbon Tetrachloride in Rats Take 36 SD rats and divide them into 6 groups (6 rats in each group), respectively: blank control group (Control), model group (Model), silymarin (positive drug control) group (purchased from Madaus AG,) the invention low dose group (GX001-1), the invention middle dose group (GX001-2.5), the invention high dose group (GX001-5). In silymarin group, 100 mg/kg daily dose of silymarin was administrated, the invention low, middle and high dose group every day respectively received to 1 ml/kg, 2.5 ml/kg and 5 ml/kg oral liquid in accordance with the example 2 cases for 5 days, Except the blank group, the other groups received carbon tetrachloride olive oil 1:1 (V/V) solution 2 ml/kg at the second, third day. All the rats were weighed and sacrificed by cervical dislocation at the sixth day, heart blood was collected and centrifuged, serum were removed to quantification of alanine aminotransferase (ALT), aspartate aminotransferase (AST) activity, total bilirubin (TB) content. A part of liver tissue were washed with ice physiological saline to remove blood, absorbed water and weighing, take part of the liver with saline ice homogenates prepared 10% liver homogenate, 4 C, 5000 rpm centrifugation for 5 min, determined total superoxide dismutase (T-SOD) activity according to instructions. A part of liver tissue were preserved in 10% buffered formaldehyde solution and then stained with hematoxylin and eosin (H and E), necrosis, hydropic degeneration, inflammatory cell infiltration and other pathological changes were observed under light microscpoe.

Figure 5:
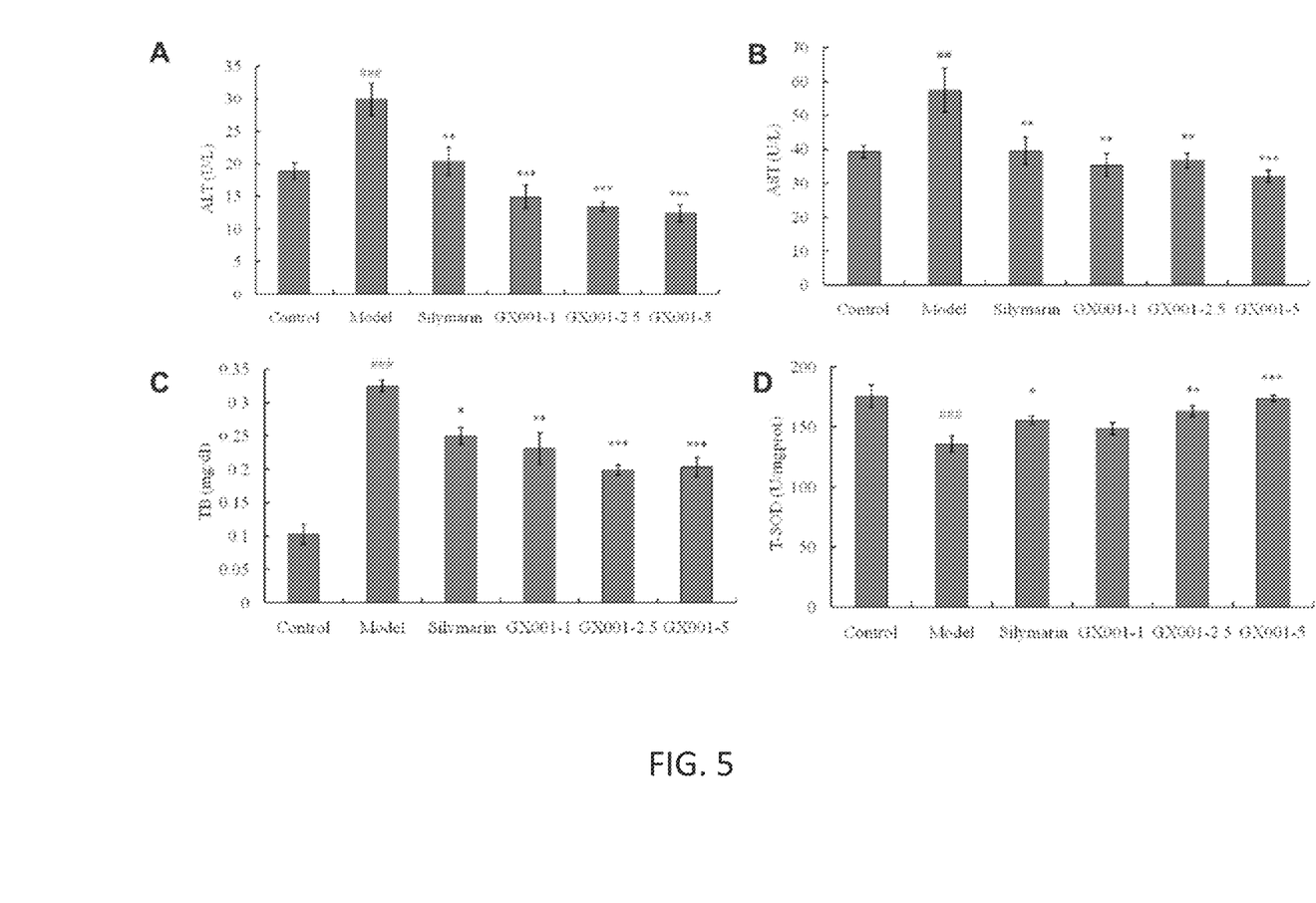
FIG. 5 shows the effect of the exemplary drug on serum and liver biochemical indexes of CCl4 induced liver injury rat model (A) serum ALT activity of CCl4 induced liver injury rat (B); serum AST activity of CCl4 induced liver injury rat (C); serum TB content of CCl4 induced liver injury rat; (D) liver T-SOD content of CCl4 induced liver injury rat.
Figure 6:
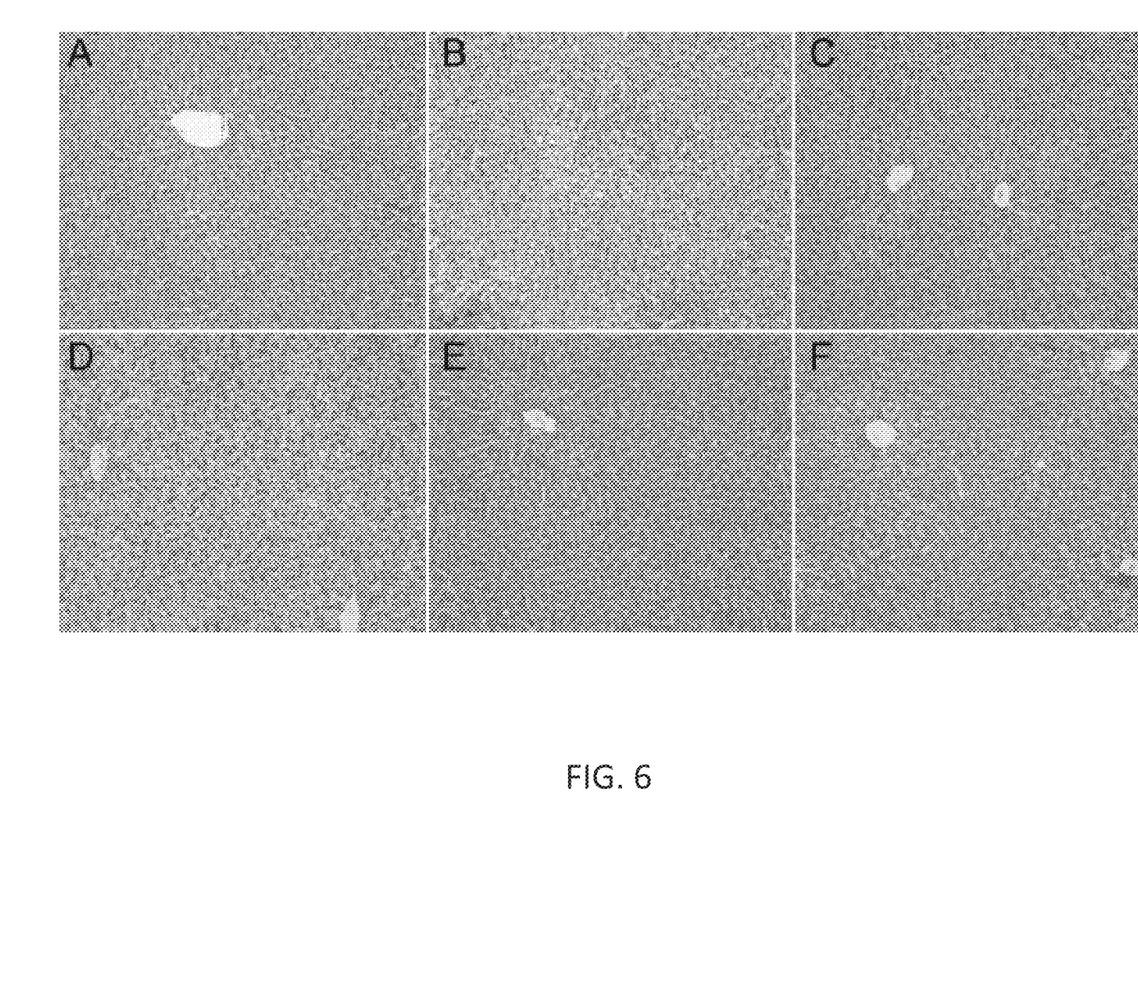
FIG. 6 shows HE staining in liver tissue of CCl4 induced liver injury rat (200×), including, (A) blank control group; (B) model group; (C) silymarin group; (D) the invention low dose group; (E) the invention middle dose group; (F) the invention high dose group.

The results are indicated in FIG. 5 and FIG. 6. As shown in FIG. 5, compared with the blank control group, in the model group, the activity of serum ALT, AST increased significantly; the content of TB significantly increased; the activity of liver T-SOD decreased significantly; compared with the model group, the silymarin group and each invention group serum ALT/AST activity decreased significantly, the TB content decreased significantly, the activity of liver T-SOD increased significantly. It indicates that The Traditional Chinese medicine oral liquid can effectively improve the liver function injury caused by carbon tetrachloride.

As shown in FIG. 6, HE staining of liver tissues of carbon tetrachloride induced liver injury rats were observed, blank control group (A) showed normal structure of hepatic lobule, hepatic plates arranged neatly, no obvious expansion of hepatic sinus, no expansion and fibrosis of portal tract, no interface inflammation, liver cell had no obvious necrosis, regeneration, degeneration; model group (B) showed disordered structure of hepatic lobule cells, hepatocyte swelling, hydropic degeneration can be observed; silymarin group (C) showed no liver cell swelling, hydropic degeneration, showed marked improvement compared with the model group; the invention low dose group (D) can be observed in less hydropic degeneration, but compared with some model group, the invention middle dose group is improved; middele dose group (E) and high dose group (F) showed complete liver plate structure, less fatty degeneration.

Example 6 the Efficacy of the Traditional Chinese Medicine Oral Liquid on Isoniazid and Rifampicin Induced Liver Injury in Rats 38 male SD rats were randomly divided into 6 groups (n=6, model group 8), respectively: blank control group (Control), model group (Model), silymarin (positive drug control) group (Silymarin), the invention low dose group (GX001-1), the invention middle dose group (GX001-2.5), the invention high dose group (GX001-5). Rats of blank control group were given 2 ml/200 g 0.3% CMC-Na for three consecutive days, starting from the fourth day to the end of fourteenth days, rats were given 3 ml/200 g 0.3% CMC Na. Except the blank control group, rat of other groups were administrated 100 mg/kg isoniazid (INH) and 100 mg/kg (RIF) of rifampicin by gavage (1 ml INH+1 ml RIF/200 g). From the fourth day to the end of the fourteenth day, the invention low, middle and high dose group every day respectively received 1 ml/kg, 2.5 ml/kg and 5 ml/kg oral liquid in accordance with the example 2, the silymarin group received 100 mg/kg silymarin daily and the model group received 0.3% CMCNa daily; 2 h after drug administration, each rat received 1 ml INH+1 ml RIF/200 g weight by gavage. After the last administration, animals were fasting 16 hours before sacrificed by cervical dislocation, but water was given, heart blood was drawn and centrifuged, serum were removed to quantification of serum alanine aminotransferase (ALT), aspartate aminotransferase (AST), alkaline phosphatase (ALP) activity, total bilirubin (TB)

content. A part of liver tissue were washed with ice physiological saline to remove blood, absorbed water and weighing, take part of the liver with saline ice homogenates prepared 10% liver homogenate, 4 C, 5000 rpm centrifugation for 5 min, determined total superoxide dismutase (T-SOD) activity and malondialdehyde (MDA) content according to instructions. A part of liver tissue were preserved in 10% buffered formaldehyde solution and then stained with hematoxylin and eosin (H and E), necrosis, hydropic degeneration, inflammatory cell infiltration and other pathological changes were observed under light microscpoe.

Figure 7:
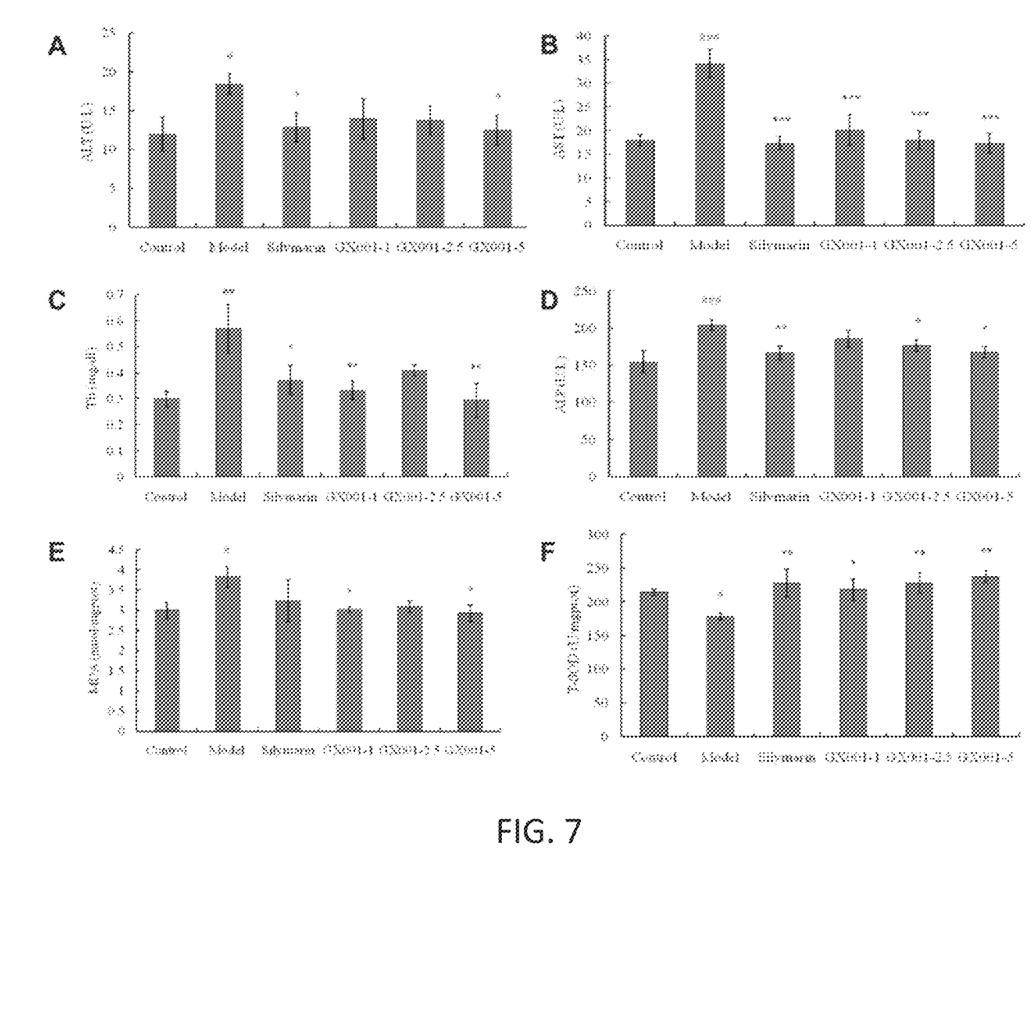
FIG. 7 shows the effect of the exemplary drug on serum and liver biochemical indexes of isoniazid-rifampicin induced liver injury rat model (A) serum ALT activity of isoniazid-rifampicin induced liver injury rat; (B) serum AST activity of isoniazid-rifampicin induced liver injury rat; (C) serum TB content of isoniazid-rifampicin induced liver injury rat; (D) serum ALP activity of isoniazid-rifampicin induced liver injury rat; (E) liver MDA content of isoniazid-rifampicin induced liver injury rat; (F) liver T-SOD activity of isoniazid-rifampicin induced liver injury rat.
Figure 8:
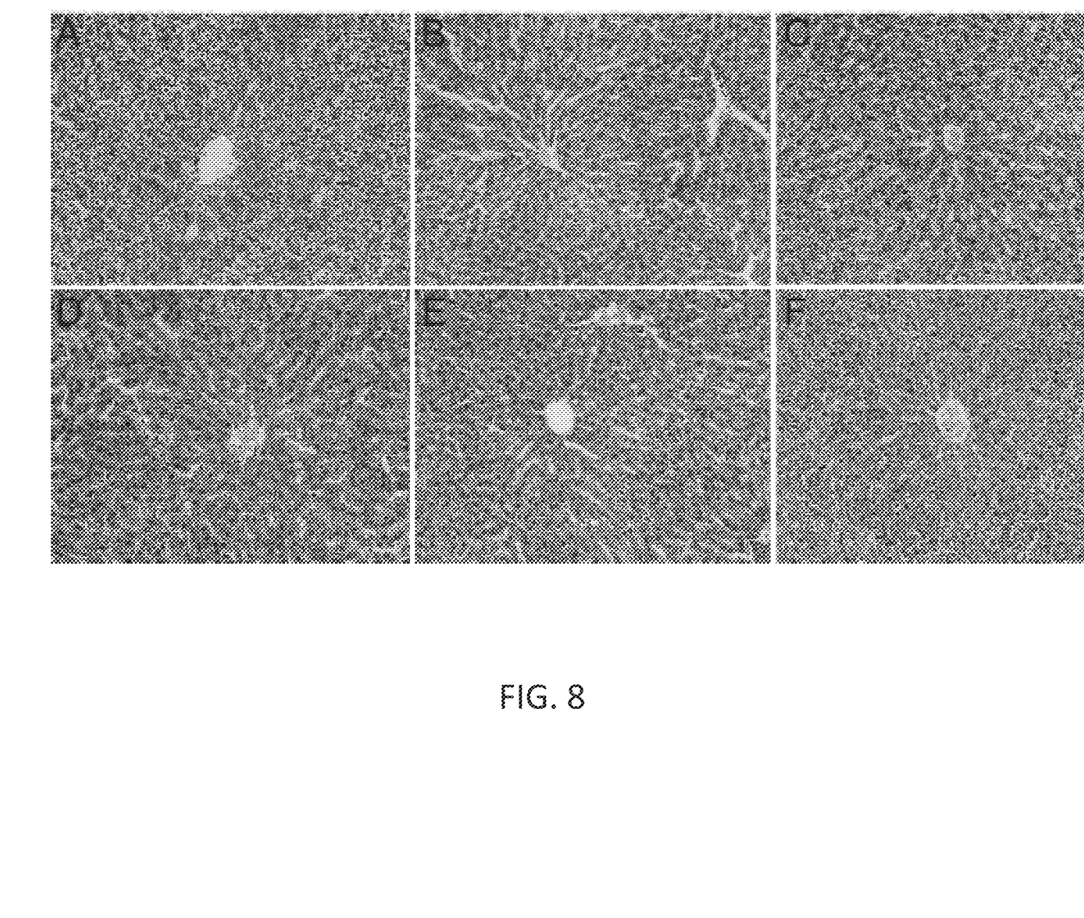
FIG. 8 shows HE staining of liver tissue of isoniazid-rifampicin induced liver injury rat (200×), including, (A) blank control group; (B) model group; (C) silymarin group; (D) the invention low dose group; (E) the invention middle dose group; (F) the invention high dose group.

The results are indicated in FIG. 7 and FIG. 8. As shown in FIG. 7, compared with the blank control group, in the model group, the serum ALT AST activity increased significantly, the TB content increased significantly, the liver T-SOD activity decreased significantly, the MDA content increased significantly; compared with the model group, rats of silymarin group and each invention group showed significantly decreased ALT/AST/ALP activity, significantly increased T-SOD activity, significantly decreased TB, MDA content, indicated that the traditional Chinese medicine oral liquid can effectively improve the isoniazid and rifampicin induced abnormal liver function.

As shown in FIG. 8, HE staining of liver tissues rats were observed, the blank control group (A) showed normal structure of hepatic lobule, hepatic plates arranged neatly, no obvious expansion of hepatic sinus, nucleus compact, liver cell had no obvious necrosis, regeneration and degeneration; model group (B) showed hepatic lobule structure disorder, cell edema, inflammatory cell infiltration, liver sinus congestion, indicated dilation of liver sinuses, the invention high dose group (F) showed the recovery of nuclear compact, sinusoidal expansion phenomenon almost eliminated.

Example 7 the Effect of the Traditional Chinese Medicine Oral Liquid on CCl4 Induced Acute Kidney Injury in Mice 40 Kunming mice were randomly divided into 4 groups (n=10): blank control group, model group, silymarin group, the invention group (group GX001). The blank control group and model group were treated with 10 ml/kg saline by gavage, the silymarin group was administrated with silymarin, the GX001 group was administrated with Chinese medicine oral liquid prepared in according to the example 2, for 10 days. 1 h After the last drug administration, except blank control group, each mice was treated with 0.1% CCl4 (vegetable oil) 20 ml/kg by intraperitoneal injection. Animal were weighted and sacrificed after 16 h of fasting. Blood was drawn and centrifuged, serum were removed to quantification of CRE (creatinine), BUN (Niao Sudan), UA (uric acid) content.

The results are shown in Table 1, compared with the control group, the content of serum UA, BUN, CRE was significantly increased in the model group (P<0.01); compared with the model group, serum CRE, BUN, UA levels were significantly decreased in GX001 group (P<0.05); only serum BUN decreased significantly in silymarin group (P<0.05).

TABLE 1

Effect of GX001 on serum of acute kidney injury model induced by CCl4 in mice ($\bar{x} \pm s$, n = 10)

| Group | Dosage | CRE (μmol/L) | BUN (mmol/L) | UA (μmol/L) |
|---|---|---|---|---|
| blank control group | — | 118.88 ± 43.70 | 14.99 ± 3.19 | 98.13 ± 12.42 |
| carbon tetrachloridemodel group | — | 243.30 ± 53.81## | 27.53 ± 5.14## | 147.11 ± 21.11## |
| silymarin group | 200 mg/kg | 208.82 ± 64.27 | 22.92 ± 4.01* | 128.36 ± 20.92 |
| GX001 group | 5 ml/kg | 191.88 ± 21.72* | 22.42 ± 3.79* | 113.76 ± 13.10* |

Relative to blank control group, ##p < 0.01;
relative to model group, *p < 0.05

Example 8 Clinical Trials of the Traditional Chinese Medicine Oral Liquid 3 consenting volunteers were given the traditional Chinese medicine oral liquid prepared in according to the example 2 orally for 60 consecutive days, 3 times a day, each time 10 mL. The TC (total cholesterol), TG (triglyceride), LDL (low density lipoprotein), HDL (High density lipoprotein) level, uric acid and fatty liver symptom parameters were determinated on day 0 and day 60 zeroth days and sixtieth days.

The results w shown in Table 2, showed that the traditional Chinese medicine oral liquid can reduce the content of cholesterol, triglyceride, low density lipoprotein and uric acid in human body, increase the content of high density lipoprotein in human body, effectively eliminate fatty liver symptoms, indicating that the oral liquid has clinical potential in protecting liver and kidney.

TABLE 2

Before and after treatment cooperation the traditional Chinese medicine oral liquid medicine

| gander/age | test time | TC (μmol/DL) | TG (μmol/DL) | LDL (μmol/DL) | HDL (μmol/DL) | UA (μmol/DL) | hepatic adipose infiltration symptom |
|---|---|---|---|---|---|---|---|
| M/48 | Before dose | 7.12 | 9.05 | 4.02 | 2.31 | 573 | ++ |
| | After dose | 5.26 | 2.62 | 2.35 | 3.35 | 399 | − |

TABLE 2-continued

Before and after treatment cooperation the
traditional Chinese medicine oral liquid medicine

| gander/age | test time | TC (μmol/DL) | TG (μmol/DL) | LDL (μmol/DL) | HDL (μmol/DL) | UA (μmol/DL) | hepatic adipose infiltration symptom |
|---|---|---|---|---|---|---|---|
| M/59 | Before dose | 6.95 | 3.76 | 3.56 | 1.35 | 468 | + |
|  | After dose | 4.96 | 2.05 | 2.35 | 2.54 | 409 | − |
| F/57 | Before dose | 5.78 | 3.58 | 4.56 | 1.68 | 497 | +++ |
|  | After dose | 4.65 | 2.11 | 3.01 | 3.06 | 386 | − | ps:
"+" mild hepatic adipose infiltration,
"++" moderate hepatic adipose infiltration,
"+++" severe hepatic adipose infiltration,
"−" no hepatic adipose infiltration.

The invention claimed is:

1. A traditional Chinese medicine composition for protecting the liver and kidney, which consists of following weight parts in crushed form:
   100-200 parts of *Polygonatum odoratum*,
   100-200 parts of *fructus lycii*,
   80-160 parts of *radix ophiopogonis*,
   70-130 parts of *Angelica sinensis*,
   70-130 parts of *semen cassiae*,
   70-130 parts of white peony root,
   70-130 parts of dried orange peel,
   70-130 parts of prepared *rehmannia* root,
   70-130 parts of *chrysanthemum*,
   30-70 parts of rhizome *chuanxiong*,
   20-40 parts of Irkutsk *anemone* rhizome and
   10-20 parts of *bupleurum*, wherein the composition is in the form of a tablet, pill, capsule, tincture, syrup and emulsion agent, liquid aerosol spray drops, injection, automatic injection device or suppository.

2. The traditional Chinese medicine composition of claim 1 wherein the composition comprises:
   volatile oil of *Angelica sinensis*, rhizome *chuanxiong*, *chrysanthemum*, *bupleurum*, Irkutsk *anemone* rhizome and dried orange peel, non-alcohol precipitation of water soluble matter of *Angelica sinensis*, rhizome *chuanxiong*, *chrysanthemum*, *bupleurum*, Irkutsk *anemone* rhizome and dried orange peel, and non-alcohol precipitation of water soluble matter of *Polygonatum odoratum*, *fructus lycii*, *radix ophiopogonis*, *semen cassiae*, white peony root and prepared *rehmannia* root.

3. The traditional Chinese medicine composition of claim 2, wherein:
   the volatile oil is prepared by mixing with water to make a water solution, and distilling the water solution to produce the volatile oil and a distilled material;
   an aqueous solution is prepared by filtering the distilled material to produce the aqueous solution and a residue;
   water extract is prepared by boiling a water solution containing the residue and remaining ingredients and retention of water solution preparation;
   the non-alcohol precipitation is prepared by increasing concentration of alcohol in a mixture of the aqueous solution and the water extract and retaining alcohol soluble substance, wherein the alcohol is ethanol.

4. A traditional Chinese medicine preparation for the protection of liver and kidney, comprising the traditional Chinese medicine composition of claim 1 and a pharmaceutically acceptable carrier.

5. The preparation of claim 4, wherein the pharmaceutically acceptable carrier is selected from the group consisting of sugar, honey, ethyl p-hydroxybenzoate and mixtures thereof.

6. In combination, the traditional Chinese medicine composition described in claim 1 and at least one drug for lowering level of cholesterol, triglyceride, low density lipoprotein, creatinine, urea nitrogen, and uric acid, for improving level of high density lipoprotein, and/or for reducing fatty liver symptoms.

7. A preparation method of a traditional Chinese medicine composition for protecting the liver and kidney, which consists of following weight parts in crushed form:
   100-200 parts of *Polygonatum odoratum*,
   100-200 parts of *fructus lycii*,
   80-160 parts of *radix ophiopogonis*,
   70-130 parts of *Angelica sinensis*,
   70-130 parts of *semen cassiae*,
   70-130 parts of white peony root,
   70-130 parts of dried orange peel,
   70-130 parts of prepared *rehmannia* root,
   70-130 parts of *chrysanthemum*,
   30-70 parts of rhizome *chuanxiong*,
   20-40 parts of Irkutsk *anemone* rhizome and
   10-20 parts of *bupleurum*,
   comprising the steps of:
   (1) smashing and mixing *Angelica sinensis*, rhizome *chuanxiong*, *chrysanthemum* and *bupleurum*, Irkutsk *anemone* rhizome and dried orange peel, adding water and performing distillation, retaining volatile oil, water solution and dregs which are not dissolved in water;
   (2) mixing dregs obtained in step (1) and *Polygonatum odoratum*, *fructus lycii*, *radix ophiopogonis*, *semen cassiae*, white peony root and prepared *rehmannia* root, and decocting the mixture with water to produce a decoction liquid, then filtering the decoction liquid to produce a filtrate, and mixing the filtrate and the water solution, concentrate, increasing the alcohol concentration, recovering a supernatant after alcohol, filtered and concentrated, as a clear paste; and
   (3) mixing the clear paste obtained from step (2) and the volatile oil obtained from step (1).

8. A traditional Chinese medicine composition for protecting the liver and kidney, which consists of following weight parts in crushed form:
   100-200 parts of *Polygonatum odoratum*,
   100-200 parts of *fructus lycii*,
   80-160 parts of *radix ophiopogonis*,
   70-130 parts of *Angelica sinensis*,
   70-130 parts of *semen cassiae*, 70-130 parts of white peony root,
70-130 parts of dried orange peel,
70-130 parts of prepared *rehmannia* root,
70-130 parts of *chrysanthemum*,
30-70 parts of rhizome *chuanxiong*,
20-40 parts of Irkutsk *anemone* rhizome and
10-20 parts of *bupleurum*, wherein the composition is prepared according to the method of claim 7.

9. A method for treatment of liver injury and/or renal injury in an individual, comprising the step of administering an effective amount of a composition which consists of following weight parts in crushed form:

100-200 parts of *Polygonatum odoratum*,
100-200 parts of *fructus lycii*,
80-160 parts of *radix ophiopogonis*,
70-130 parts of *Angelica sinensis*,
70-130 parts of *semen cassiae*,
70-130 parts of white peony root,
70-130 parts of dried orange peel,
70-130 parts of prepared *rehmannia* root,
70-130 parts of *chrysanthemum*,
30-70 parts of rhizome *chuanxiong*,
20-40 parts of Irkutsk *anemone* rhizome and
10-20 parts of *bupleurum*,
to the individual.

* * * * *